United States Patent [19]

Markert

[11] Patent Number: 4,764,990
[45] Date of Patent: Aug. 23, 1988

[54] VENTILATED FACE SHIELD

[76] Inventor: Allan R. Markert, 138 E. Sims, St. Paul, Minn. 55117

[21] Appl. No.: 948,113

[22] Filed: Dec. 31, 1986

[51] Int. Cl.$^4$ .............................................. A61F 9/04
[52] U.S. Cl. ........................................ 2/429; 2/436; 2/9; 128/201.15; 128/206.24
[58] Field of Search ................... 2/424, 425, 427, 428, 2/429, 430, 436, 437, 206, 9; 128/201.15, 206.12, 206.21, 206.23, 206.24, 201.22, 201.23

[56] References Cited

U.S. PATENT DOCUMENTS

| | | | |
|---|---|---|---|
| 1,176,901 | 3/1916 | Jessup | 128/201.23 |
| 1,348,819 | 8/1920 | Miller | 128/201.15 |
| 2,314,889 | 3/1943 | Manson et al. | 128/201.23 |
| 2,344,920 | 3/1984 | Maggi | 128/201.25 |
| 2,642,574 | 6/1953 | Eloranta | 2/427 |
| 2,665,686 | 1/1954 | Wood et al. | 128/206.12 |
| 2,818,857 | 1/1958 | Wilkins et al. | 128/206.28 |
| 2,891,541 | 6/1959 | Tietze | 128/201.15 |
| 2,898,908 | 8/1959 | Sovinsky | 128/201.15 |
| 3,020,911 | 2/1962 | Girosn | 128/201.15 |
| 3,152,588 | 10/1964 | Rogowski | 128/206.12 |
| 3,220,408 | 11/1965 | Silverberg | 128/206.23 |
| 3,315,673 | 4/1967 | Morton, Jr. | 128/206.23 |
| 3,680,555 | 8/1972 | Warncke | 128/201.15 X |
| 4,083,065 | 4/1978 | Warncke | 2/424 |
| 4,296,746 | 10/1981 | Mason, Jr. et al. | 128/206.12 X |
| 4,354,285 | 10/1982 | Rudd | 2/424 |
| 4,524,465 | 6/1985 | Huber | 2/436 X |
| 4,538,303 | 9/1985 | Schnitzler | 2/425 X |

FOREIGN PATENT DOCUMENTS 2564709 11/1985 France ................................... 2/425
2115293 9/1983 United Kingdom ........... 128/201.15

Primary Examiner—Peter Nerbun
Attorney, Agent, or Firm—Merchant, Gould, Smith, Edell, Welter & Schmidt

[57] ABSTRACT

A mask arrangement particularly adapted for use in cold weather conditions includes a mask member and a spaced eye shield. Air flow directing means directs air flow between the eye shield and the mask member, providing comfortable air flow and inhibition to fogging of the eye shield. The mask member is divided into a vision region and a breathing region. The vision region includes a port therein covered by the eye shield. The breathing region is generally isolated from the vision region and includes a breathing aperture with baffle means associated therewith. In a preferred embodiment, the breathing aperture comprises a large aperture in the central portion of the breathing region, with the baffle means comprising a baffle plate mounted over the breathing aperture. The baffle plate generally deflects air preventing jetting directly into the mouth of the wearer. Relative constant spacing between the eye shield and the mask member facilitates air flow without substantial turbulence.

9 Claims, 3 Drawing Sheets

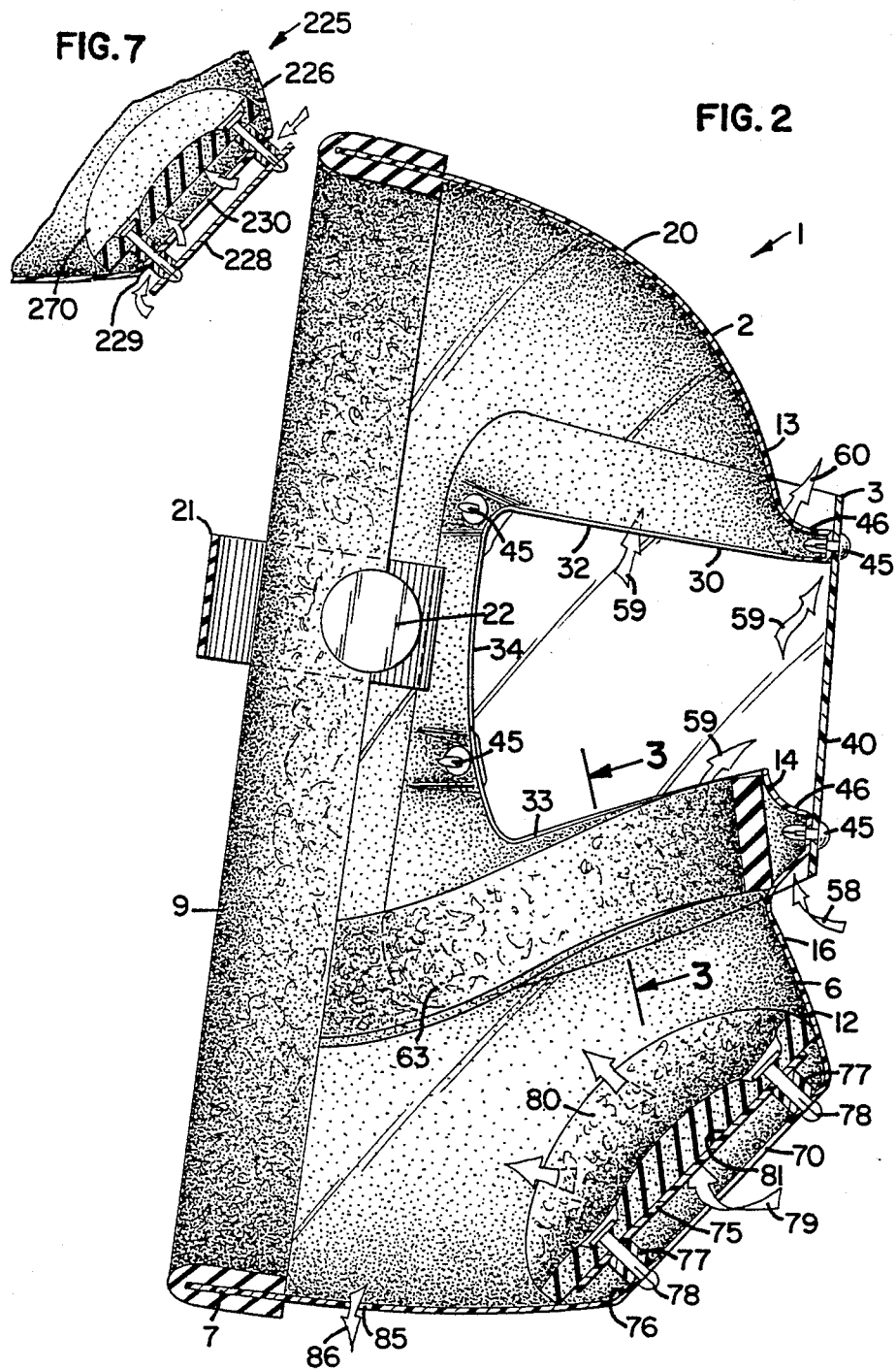

VENTILATED FACE SHIELD

TECHNICAL BACKGROUND

The present invention relates to masks and in particular to protective masks used to shield a wearer's eyes and face from the environment. Most particularly, the invention concerns cold weather masks. However, the principles disclosed herein may be readily adapted for use in a variety of applications including in masks for wearing under hazardous working conditions.

BACKGROUND OF THE INVENTION

A very wide variety of protective masks and features for association therewith are known. A major categorical breakdown of such masks is into the soft-walled type and the substantially rigid walled type.

The soft-walled type of mask, for example masks formed from knitted materials, fabrics or the like, generally press against substantial portions of the face of the wearer. This may be uncomfortable for many wearers, and may irritate sensitive portions of a wearer's face. Such masks are often used for protection from cold weather, winds, and the like; for example as ski masks. The masks are usually foldable, collapsible, or otherwise formable so that they may be stored in a wearer's pocket or the like. Such masks, and features thereof, are generally not of substantial concern to the features of the present invention.

The present invention more directly concerns substantially rigid masks. Such masks usually include a face piece or mask member, which is worn against a wearer's face to cover same. The masks usually have a rigid topography pre-formed through the utilization of a relatively rigid material such as leather or plastic. The masks are generally retained upon the head of the wearer by means of head straps or the like.

In some conventional arrangements relatively rigid masks may include two regions or sections: a breathing region; and, a vision region. The breathing region generally covers or concerns the wearer's mouth, or nose and mouth. The vision region generally includes an eye piece or shield, to protect the wearer's eyes from the elements. In conventional arrangements, the breathing region and vision region may be isolated from one another, or they may form communicating volumes of space positioned between the mask member and the wearer's face.

In general conventional mask arrangements have been plagued with, or have been concerned with, the following types of features and problems. First, there is the problem of providing adequate ventilation for breathing. In some instances, the mask may be intended to permit inhalation of air directly from the environment, and in other instances isolated air supplies are intended. Provision of an adequate seal between the mask and the wearer's head or face has been of some concern.

Another feature of some concern has been the provision of adequate vision means. Here, several factors have been of interest including: inhibition of fogging along the inside of the vision surface, which results from warm moist air inside of the mask, between the mask and the wearer's face; provision of adequate peripheral vision for the wearer; provision of undistorted views to the wearer; a combination usable by eye glass wearers; provision of reinforcement for protection against flying objects and the like; provision of protection against excessive glare or light; replaceability of portions covering the vision area of the mask, so that should same become scratched, blocked or otherwise unclear, replacement is possible; and, comfort.

With respect to the breathing portion of such mask, several problems and features have been of concern including: provision of means protecting the wearer against breathing of uncomfortably cold, dry, external air; comfort without claustrophobic feeling; provision of filter means or the like to filter incoming air; provision of means for ease of replaceability of such filter means; isolation of breathing air from air in the vision portion of the apparatus; provision of means inhibiting excessive ice or frost formation over the mouth area, inhibiting free breathing; and, provision of means permitting a wearer to speak without interference by portions of the apparatus.

Protective face masks may be worn under a variety of conditions. For example, a mask might be desired for routine wear during exposure to cold temperatures, high winds or the like. Also, the wearer may be utilizing the mask in association with high speed travel such as on a snowmobile, bob sled, ice boat, motorcycle or the like. On the other hand, the wearer may be utilizing the mask during working operations, such as during welding, wood-working or the like. The mask might be used when exposure to particulate matter such as dust or dirt is anticipated. Few, if any, masks have been designed which are readily adaptable to such a wide variety of uses, or environments.

Further, masks utilizable under conditions of heavy winds, generated either by the environment or movement of the wearer through the environment, as for example on a snowmobile, may require special features. A reason for this is the substantially great air flow which may be directed against the front or face portion of the mask. Should the mask be inappropriately designed, the wearer may have difficulty retaining his or her head in a comfortable position against the force of the winds. Also, the winds may make breathing difficult, due to a jetting flow directly into breathing apertures or the like.

Another problem with conventional arrangements has been the provision of seal means between the mask member and the face to accommodate various facial shapes readily and to retain moisture and warmth.

In some instances it may be desirable to wear the mask in association with a hood, hat, cap, helmet or the like. Conventional arrangements of masks have not readily adapted for this use in a satisfactorily convenient and comfortable manner.

It would be preferred that in a mask designed to accommodate the above types of features and problems, the features be embodied in an arrangement relatively easy to manufacture and maintain. Further, projecting members or mechanisms are preferably avoided, as they may: encumber the mask becoming potentially harmful projections; and, create uncomfortable arrangements, or unattractive features. Thus, in the mask art it is a substantial improvement to provide features accommodating the discussed problems and arrangements in a simplified, convenient, and attractive manner.

OBJECTS OF THE INVENTION

Therefore, the objects of the invention are: to provide a mask arrangement including a mask member, an eye shield and means for inhibiting fogging of an inner surface of the eye shield; to provide such an arrangement where the mask member includes a vision region and a breathing region, isolated from one another by seal means; to provide such an arrangement wherein the vision region includes a large open vision port therein, covered by an eye shield mounted thereover and spaced from the mask member; to provide such an arrangement including air flow directing means for directing a portion of air flow against the mask underneath the eye shield to inhibit fog formation along an inner surface of same; to provide such an arrangement wherein the air flow directing means generates the desired air flow underneath the eye shield without substantial discomforting turbulence; to provide such an arrangement wherein a breathing aperture is provided in the breathing region, to permit inhalation by a wearer of air external to the mask; to provide such an arrangement wherein baffle means may selectively be provided in association with the breathing aperture to direct air flow into the aperture in such a manner as to avoid a jetting of air directly into a wearer's mouth or nose; to provide such an arrangement wherein the breathing region optionally includes a moisture retaining filter therein, to facilitate comfort and ease of breathing; to provide such an arrangement wherein the breathing arrangement includes a drain aperture therein, to allow excessive condensation forming on an inner surface of the breathing surface to drain from the mask member without substantial discomfort or inconvenience; to provide such an arrangement wherein the eye shield is mountable by mounting means including a mechanism permitting ease of removal, remounting, or replacement; to provide such an arrangement wherein the eye shield may be tinted, polarized or otherwise adapted for protection of a wearer from glare; to provide such an arrangement wherein the eye shield comprises a single elongate shield member mounted in an overlapping engagement with the vision port; to provide such an arrangement wherein the eye shield includes an upper edge spaced from the mask member a relatively constant distance therealong, in order to facilitate air flow without substantial turbulence; to provide such an arrangement wherein preferably the breathing region may be selectively separated from the vision region by means of a compressible seal formed in a substantially chevron shape, having first and second extensions oriented to engage a wearer's nose along sides thereof, substantially adjacent a wearer's cheek; to provide such an arrangement including a forehead dome cover, for extending over the forehead portion of a wearer; to provide an arrangement having no forehead dome portion, but rather an elongate extension of horizontal upper edge facilitating wearing of the arrangement in operative combinations with a helmet or the like; to provide such an arrangement which may be comfortably worn in high winds or the like; to provide such an arrangement wherein the air flow directing means comprises first and second elongate concave portions positioned in said mask member substantially beneath a vision port thereof, to receive air flow and direct same behind and over said eye shield; and to provide such a mask arrangement which is relatively inexpensive to produce, which is relatively simple to use, which is particularly well adapted for the proposed uses thereof.

Other objects and advantages of this invention will become apparent from the following descriptions, taken in connection with the accompanying drawings, wherein are set forth by way of illustration and example certain embodiments of the invention.

SUMMARY OF THE INVENTION

A mask arrangement is provided for protecting a wearer's face during use. Generally, the mask arrangement is designed for offering protection from high winds and cold weather. However, it may be readily adapted for utilization as a protective mask during indoor use, as for example in the work place.

The mask arrangement is formed from a relatively rigid material and includes a mask member having a central portion and an outer periphery. The outer periphery is adapted to engage a wearer's head or face, mounting the mask thereon. Seal or gasket means may be provided in association with the outer periphery, to provide for a comfortable sealing engagement between the mask arrangement and the wearer. Preferred sealing may be by means of a foam liner, or other compressible liner, along the mask member outer periphery. Preferably the outer periphery terminates in front of a wearer's ears. This facilitates comfort and unencumbered hearing. Further, as a result, the arrangement does not interfere with many conventional ear coverings.

The central portion of the preferred mask member is divided into two basic regions: a vision region and a breathing region. The rigid construction permits spacing between the central portion and a wearer's face, which facilitates comfort to the wearer. Two major reasons for this are: that air is permitted to circulate over much of the face of the wearer; and, the rigid construction permits retention of much of the structure spaced from the wearer's face. Also, spacing and insulation between the wearer's face and the central portion of the mask member is further facilitated by the insulating foam liner. The breathing region is in engagement with a wearer's nose and mouth, and is that portion of the mask which generally includes inhaled and exhaled air. The vision region, on the other hand, is positioned above the breathing region, when the mask arrangement is worn. The vision region is that portion of the mask through which a wearer views.

For the preferred embodiment, the vision region and viewing region are separated from one another by seal or gasket means. The preferred seal means comprises a foam or other compressible liner positioned along an inside surface of the mask member, to abut against a wearer's face. The preferred seal means for this region comprises a chevron-shaped extension of seal centered generally around a nose bridge portion of the mask member. The chevron-shaped seal includes first and second portions extending along an inner surface of the mask member toward the mask member outer periphery. Preferably, the first and second extensions of the seal each are oriented to abut sides of a wearer's nose and extend therealong, substantially adjacent a wearer's cheeks. In this manner a comfortable, effective seal may be provided. Further, insulation is facilitated between the wearer's face and the mask. This is a manner in which the preferred embodiment of the present invention differs from many previous arrangements. In some prior arrangements the seal abutted the wearer's nose along the soft, fleshy part of the lower part of the nose and nose bridge. This could be uncomfortable, could be inefficient as a comfortable seal, and could make utilization of a single mask by faces of a variety of shapes somewhat more difficult. It will understood that the seal need not be air tight, but rather will be effective as long as excessive air flow between the vision region and the breathing region are avoided. Generally, if a permeable seal such as a foam seal is used, it will be understood that warmth and moisture may build up therein during use so that any air flowing therethrough to the breathing region will be somewhat warmed and humidified before it is inhaled by the wearer. As used herein, the term "inner side" or variants thereof refer to the side of the mask arrangement toward a wearer's face during use. The opposite side is referred to herein as the "outer side".

The mask member may be mounted upon a wearer by means of a head strap or the like, anchored to opposite sides of the mask. The head strap may be an elongate, elastic or other expandable type member, readily adapted for stretching over a wearer's head, hood, hat or the like. In the alternative, an adjustable belt or the like may be used. Further, the mask may be mounted in association with a hood, helmet or other protective gear in engagement therewith.

The mask arrangement includes an open vision port in the vision region thereof. Generally, the vision port comprises an elongate aperture in the vision region, exposing the wearer's eyes. In the preferred embodiment, the vision port is a single large aperture, facilitating a wide field of view; however a multiple apertured arrangement may be utilized in association with the principles of the present invention.

The mask arrangement includes an eye shield mechanism including an eye shield mounted thereon in association with the vision port. While either a single piece or multiple piece eye shield may be utilized in association with many of the principles of the present invention, the preferred embodiment utilizes a single eye shield, sufficiently transparent or opaque to be used for viewing purposes. The preferred eye shield has an upper edge, a lower edge, side edges, an inner surface and an outer surface. The inner surface is that surface which faces the wearer, the outer surface being the opposite.

The eye shield is mounted by associated mounting means, to extend over the vision port and on the exterior surface of the mask member. Preferably, the eye shield is spaced from the mask member, by spacing means. As a result, the vision region of the mask member is well ventilated. This helps inhibit condensation or fogging along the inner surface of the eye shield, a substantial problem in many mask arrangements.

The preferred mounting means for the eye shield is constructed and arranged to facilitate ready attachment or disattachment of the eye shield, with respect to the mask member. As a result, the eye shield may be easily dismounted and cleaned. Further, the eye shield may be readily replaced should it become damaged, or should it become desirable to utilize a different type of eye shield. Various types of eye shields may be utilized in association with the invention including: tinted eye shields; polarized eye shields; particularly fracture-resistant eye shields; and prescription eye shields. In some embodiments, the eye shield may be adapted to permit the arrangement to be utilized as a welder's mask. An optional eye shield includes a dust or particle filter along an outer edge thereof.

The preferred mask arrangement includes a sufficiently large vision region to accommodate use by wearers of corrective eye glasses or the like. Comfort to such persons is facilitated by the spacing between the eye shield and the mask member. Further, the large ventilation space will help prevent fogging on the wearer's own corrective eye glasses.

The preferred mask arrangement also includes a pair of elongate, concave, longitudinal channels extending in opposite directions from a nose bridge portion of the mask. The channels preferably extend along, and underneath, the vision port. Preferably, the longitudinal channels also extend generally along a lower edge of the eye shield. The longitudinal channels comprise part of an air flow directing means, yielding a unique advantage of the present invention.

Should the mask be worn in high winds, or by a rider of a snowmobile or the like, air directed against the front of the mask will at least partially flow into the concave longitudinal channels. These channels will tend to deflect air flow upwardly behind the eye shield, generally against an inner surface of same. The air flow will then, in general, come out from behind the eye shield in a path of flow extending upwardly from the eye shield upper edge. Thus, the air flow is generally directed between the eye shield and the wearer's face, and preferably against the eye shield inner surface. This air flow will tend to prevent fogging or condensation along the eye shield inner surface. Further, the air-flow directing means provides an air flow channel facilitating comfortable wear.

Preferably, the eye shield is mounted on the mask member in such a manner that the eye shield upper edge is spaced a relatively constant distance from the mask member. In this manner, turbulence in air flow behind the eye shield is kept relatively low, facilitating comfort to a wearer. That is, it helps prevent turbulence in the air flow which could otherwise be directed against a wearer's eyes to cause discomfort. Preferably, the eye shield is symmetrically mounted on the mask member, again to inhibit turbulence formation in the air flow.

A preferred spacing of the eye shield from the mask member, along the eye shield upper edge, is between about ¼ inch and about ½ inch. With such a spacing it has been found that relatively smooth air flow results, with little bothersome turbulence and also with adequate ventilation for effective operation of the arrangement.

As indicated previously, the breathing region of the preferred embodiment is adapted to cover a wearer's nose and mouth. Aperture means provided in the breathing region permits air flow into the mask from the exterior environment. The preferred aperture means comprises a single aperture centrally located in the breathing region of the mask member, through which a wearer can inhale and exhale.

An advantage to the present invention is the selective provision of baffle means in association with the aperture means, directing air flow. Generally, in the absence of a baffle means air flow into the aperture means may generate an undesired jetting effect. That is, in the absence of such a baffle means and under high winds, either resulting from windy weather or movement of a wearer at high speed through the air, the air may tend to jet into the aperture, forcing cold air directly against the wearer's face, generating discomfort and a potentially unhealthy situation. The baffle means are preferably mounted in association with the aperture means, to generally deflect air moving into the aperture means and lessening any such jetting effect. Preferred baffle means comprise a plate or shroud mounted on either an inner surface or an external surface of the breathing region, generally to overlap or cover the aperture means. The baffle, or baffle plate, would then deflect incoming air. While baffle means are provided in association with the preferred embodiment, in many uses a baffle will not be desired and the mask arrangement may selectively be prepared without a baffle, or with a removable baffle.

The preferred embodiment includes within the breathing region, a heat and moisture retaining means. Generally this is provided by filter means situated between a wearer's mouth and the breathing aperture means. Such a heat and warmth retaining means may be, for example, a porous filter mounted within the assembly.

Condensation from the wearer's breath is at least partially retained by the filter. This tends to warm and moisten incoming air, facilitating breathing with comfort. Preferably, the filter means is mounted to be readily replaceable as desired. Such a filter may be mounted in the absence of baffle means, with retention of many of the advantages of the present invention.

Under some conditions, excessive condensation may build up in the breathing region of the apparatus. To facilitate drainage of such condensation, without discomfort and inconvenience, a drain aperture is positioned in a lower part of the breathing region. Condensation flowing thereout will substantially not inhibit freedom of the wearer to speak, breathe, or otherwise operate while wearing the mask. Should the condensation freeze in the area of the drainage aperture, it may be relatively easily cleared away. An advantage to this is that excessive frost or ice in front of the wearer's mouth is avoided. Such a frost or ice buildup, in conventional arrangements, can encumber breathing or excessively muffle a wearer's speech.

Preferably, the breathing region is sized sufficiently to accommodate the wearer's mouth without blockage of ease of speech. This will be understood from reference to the drawings, and is one of the particular advantages of the present invention.

As suggested previously, particle filter means may be associated with an optional form of the eye shield. Such means may include, for example, a porous filter extending around an outer edge of the eye shield, between the eye shield and the mask member. Such an arrangement will help protect the wearer's eyes from dirt, dust or other particulate matter that might otherwise flow into the region between the eye shield and the mask member. Preferred filter means are sufficiently porous to permit the air flow directing means to at least partially operate in keeping the inner surface of the eye shield free from fogging or condensation.

While the rigid mask member may be formed in a variety of shapes, an advantage to the present invention is that one fairly standard shape, that shape shown in the drawings, may accommodate a variety of shapes of faces with effective utility. The rigid mask member may be formed from plastic or the like, by any of a variety of means including injection molding or vacuum molding. If desired, the material may be transparent, or may be tinted or otherwise colored. Decoration means may be associated with the mask member. This may include, for example, coloration of the mask member or molded designs therein.

As illustrated in the drawings, two basic embodiments of the present invention are described herein. In the first, the mask member includes a forehead dome portion, which can wrap substantially over the forehead of a wearer, protecting same. This version may be termed the "full face" version. In the second embodiment, the mask member includes a truncated, substantially horizontal, upper edge which overlaps a wearer's forehead in a central region thereof. The second embodiment is particularly adapted for wearing in association with a helmet or the like, as for example, during snowmobiling or ice boating.

Also as illustrated in the drawings, a variety of aperture means may be utilized in the breathing region of the arrangement. The preferred aperture means, as indicated above, is a single, relatively large, aperture positioned centrally in the mask member breathing region. On the other hand, a plurality of apertures, such as slits, or a grid pattern may be used.

It will be understood that an outer periphery of the mask according to the present invention may include attachment means thereon, facilitating attachment use in association with a hood or the like worn over a wearer's head and ears. Attachment may, for example, be by means of snaps or the like.

The drawings constitute a part of the specification and include exemplary embodiments of the present invention, illustrating various objects and features thereof. In some instances material thicknesses may be shown exaggerated, to facilitate an understanding of the drawings and the invention.

BRIEF DESCRIPTION OF THE DRAWINGS

FIG. 2 is an enlarged side cross-sectional view taken generally along line 2—2, FIG. 1.

FIG. 7 is an enlarged, fragmentary side cross-sectional view of a third alternate embodiment of the present invention, taken generally from a point of view analagous to that used for the view shown in FIG. 2.

DETAILED DESCRIPTION OF THE PREFERRED EMBODIMENT

As required, detailed embodiments of the present invention are disclosed herein; however, it is to be understood that the disclosed embodiments are merely examplary of the invention, which may be embodied in various forms. Therefore, specific structural and functional details disclosed herein are not to be interpreted as limiting, but rather as a basis for the claims and as a representative basis for teaching one skilled in the art to variously employ the present invention in virtually any appropriately detailed structure.

Figure 1:
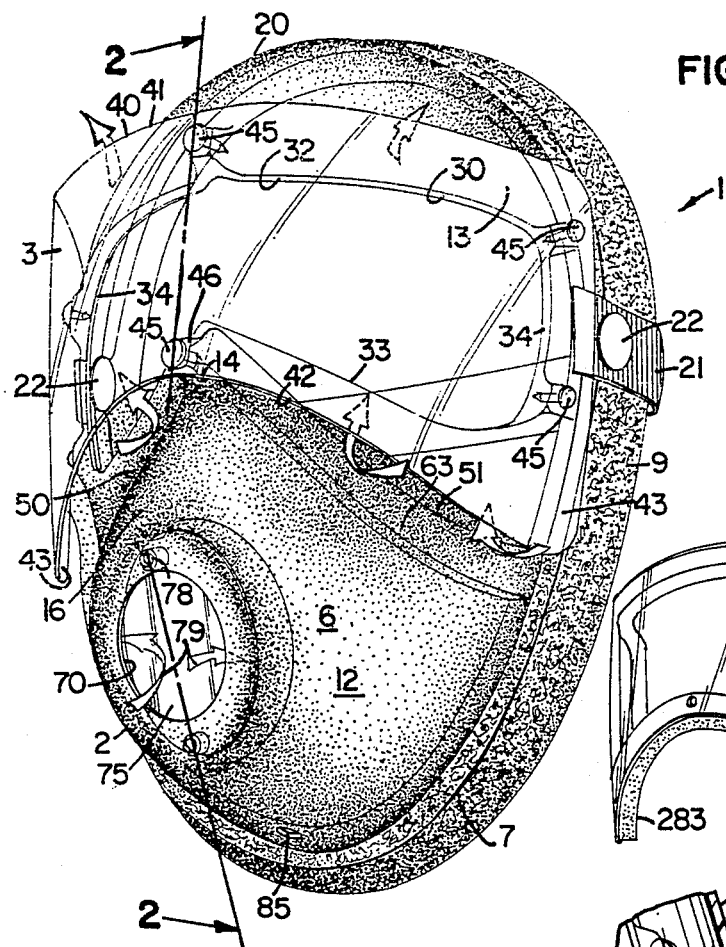
FIG. 1 is a perspective view of a mask arrangement according to a preferred embodiment of the present invention.

The reference numeral 1, FIG. 1, generally designates a mask arrangement according to the present invention.

The mask arrangement 1 includes a mask member 2 and an eye shield or portion 3. In FIG. 1, stippling as shading is used to represent much of the mask member 2. The stippling is used to help differentiate the mask member 2 from the eye shield 3, both of which are substantially transparent in the preferred embodiment shown. It will be understood that the mask member 2 may be transparent, shaded or colored, depending upon the particular application. In the Fig., stippling is also used to show gasket or seal members, as described below. In FIG. 1, a baffle, described below, in a lower front portion of the mask arrangement is shown without stippling.

The preferred mask member 2 is relatively rigid, being composed of plastic or the like. The mask member 2 may be formed from various molding techniques including vacuum molding or injection molding, depending upon the application. It will be understood from the drawings and the instant description that the primary features of the mask member are such as to permit relatively easy manufacture, utilizing a variety of conventional molding techniques.

Referring to FIG. 1, the mask member 2 includes a central portion 6 and an outer periphery 7. The outer periphery 7 may include means associated therewith facilitating a sealing engagement with the face and head of a wearer. In the embodiment shown in FIG. 1, the sealing means comprises a soft compressible seal member or gasket 9 mounted to extend completely along the mask member outer periphery 7. The seal member 9 may be, for example, a porous foam member. Such a member will comfortably engage a wearer's face, neck and head, while maintaining a snug engagement between the mask arrangement 1 and the wearer. This will help retain warm air inside of the mask 1, and facilitate comfort. Further, the seal member 9 acts as an insulation between a cold mask member 2 and the wearer's face.

Figure 3:
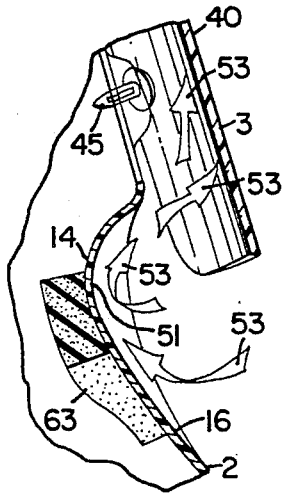
FIG. 3 is an enlarged, fragmentary cross-sectional view taken generally from the point of view of line 3—3, FIG. 2.

For the preferred embodiment, FIGS. 1 through 3, the mask member outer periphery 7 is shaped to terminate in front of a wearer's ears. In this manner, the wearer's ears are left accessible for covering by hats, ear muffs or the like. Further, the mask arrangement 1 does not substantially interfere with hearing.

The mask member central portion 6 includes a breathing region 12 and a vision region 13, FIG. 2. The vision region 13 generally covers the wearer's eyes, whereas the breathing region 12 is associated with the wearer's nose and mouth.

For the preferred embodiment, FIGS. 1 through 3, the breathing region 12 includes a nose bridge portion 14 therein. The nose bridge portion 14 generally extends outwardly from the mask arrangement 1, to extend over the wearer's nose. Preferably, the nose bridge portion 14 extends into communication with a projecting portion 16 of the mask member 2, which extends over a wearer's mouth, leaving plenty of room for ease of speech.

For the embodiment shown in FIGS. 1 through 3, the mask member 2 includes an upper forehead covering dome 20 thereon. The dome 20 extends generally over the forehead of a wearer, covering same. In this manner, the arrangement of FIGS. 1 through 3 differs from that of the alternate embodiment shown in FIGS. 4 and 5.

The mask member 2 includes retaining means associated therewith, for retaining the mask arrangement 1 on the face and head of a wearer. For the preferred embodiment, FIG. 1, the retaining means comprises an expandable strap 21 mounted on the mask member outer periphery 7. For the embodiment shown in FIG. 1, the strap 21 is mounted by means of connectors 22. However, it will be understood that a variety of means of accomplishing this mounting may be utilized in association with the principles of the present invention. Further, the strap 21 may be of a variety of types including not only expandable arrangements, but also belt and buckle type arrangements, or snap arrangements.

The vision region 13 of the mask member 2 includes a vision port 30 therein. The vision port 30 of the preferred embodiment is a large open aperture in the vision region 13. The vision port 30 generally exposes the region of a wearer's face near the wearer's eyes, to the exterior. That is, the mask member 2 does not itself cover these regions of a wearer. It will be understood that although for the preferred embodiment the vision port 30 is shown comprising a single such aperture, a multiple aperture vision port may be utilized in association with the principles of the present invention. The term "vision port", as used herein, is not intended to be limiting with respect to the number of apertures positioned in the vision region 13, although advantages from ease of construction and uninterrupted viewing may result from a single viewing aperture or vision port 30. Preferably the vision port 30 is sufficiently large to yield wide peripheral viewing. The preferred vision port 30 generally includes an upper edge 32 a lower edge 33 and side edges 34.

The mask arrangement 1 of the present invention has eye shield 3 mounted substantially over the vision port 30, and spaced therefrom. The preferred eye shield 3 is an elongate, curved shield 40 which extends substantially completely over the vision port 30, protecting same from direct exposure to winds or flying particulate matter. The shield 40 includes an upper edge 41, a lower edge 42, and side edge portions 43. Preferably shield 40 is sufficiently transparent or opaque to permit easy viewing therein. The shield 40 may be tinted, polarized or otherwise modified for preferred use under various circumstances, including to control glare. If appropriately structured, for example, the shield 40 may be used to reduce glare from sunlight or to protect a user from the glare of a welder's torch.

The shield 40 is mounted by mounting means including a spacer arrangement, so that the shield 40 is spaced a substantial distance away from much of the mask member central portion 6, FIG. 2. Preferably, the mounting means includes means permitting the shield 40 to be readily removed, remounted and/or replaced. For the embodiment shown in FIGS. 1 through 3, this is accomplished by utilization of a plurality of friction pins 45 positioned along an outer periphery of the shield 40. The friction pins 45 attach the shield 40 to mounts such as projections or supports 46 in the mask member 2. The pins 45 may be readily disconnected from the mask member 2, by force pulling away from the mounts 46. This allows shields of differing tint to be used as selected.

For reasons that will be understood from the below description, it is preferred that the shield's upper edge 41 be spaced a substantial distance apart from the mask member 2, and further that the distance remain relatively constant across the entire extension of the upper edge 41. A preferred distance is between about $\frac{1}{4}$ inch and $\frac{1}{2}$ inch, a gap size which provides good ventilation and desired air flow. A variety of distances may be utilized in association with many of the principles of the present invention.

The preferred mask arrangement 1 has a vertical plane-of-symmetry extending substantially through a center thereof, generally indicated in FIG. 1 by line 2—2.

The mask member 2 includes air flow directing means therein, to direct air flow across certain portions of the mask arrangement 1 in a preferred manner. Referring to FIGS. 1 and 2, the air flow directing means of the preferred embodiment comprises a concave surface area in mask member 2, which directs air flow behind the shield 40; i.e. against an inner surface of the shield 40, which faces a wearer's eyes. Preferably, the concave surface portion includes first and second concave extensions 50 and 51 positioned on opposite sides of the nose bridge portions 14 and extending generally therefrom toward the mask outer periphery 7. The concave extensions 50 and 51 each generally align lower edge 33 of the vision port. As a result of the concave extensions 50 and 51, air directed against a front or outside surface of the mask member 2 will be partially deflected between the eye shield 3 and the mask member 2 and a wearer of the mask arrangement 1. The concave extensions 50 and 51 will be perhaps best understood by reference to FIG. 3, which shows extension 51 in cross-section. In FIG. 3 arrows 53 indicate general air flow, as described below.

Referring to FIG. 2, air forced in the general direction of arrow 58 will be deflected into the space between the shield 40 and the mask member central portion 6 along the general path of arrows 59. This wind force will generally sweep across an inner surface of the shield 40 and come out along the shield upper edge 41 in the general path indicated by arrow 60. Such an air flow generally helps sweep the region along the inner surface of the shield 40, keeping same free from fogging or moisture buildup thereon, which is often a problem with conventional mask arrangements.

A smooth air flow is facilitated by a relatively constant or even spacing of the shield 40 from the mask member 2, especially along the shield upper edge 41. Thus a fairly laminar flow, rather than an excessively turbulent flow, generally occurs. This helps to prevent disturbance of a wearer's eyes, and to prevent direct air flow against a wearer's eyes. Further, the channeled air flow, generated by the air flow directing means, helps the wind flow across the front of the mask arrangement to occur with ease. That is, a person wearing the mask arrangement 1 may more easily cut through the wind.

To facilitate air flow over the mask arrangement 1, preferably the mask arrangement is aerodynamically designed with appropriate curved surfaces. This is generally accomplished by the preferred arrangement, as indicated in FIGS. 1 and 2.

The preferred mask arrangement 1 includes seal means therein generally separating the breathing region 12 from the vision region 13. The seal means generally comprises a compressible member or gasket 63 which seals between a wearer's face and an inner surface of the mask member 2. The compressible member 63 may, for example, be composed of a flexible porous foam member or the like. Such a seal generally isolates the breathing region 12 from the vision region 13, to prevent substantial loss of warm moist air from the breathing region 12, to the open vision region 13.

The preferred seal member 63, according to the present invention, is positioned in the inner surface of the mask member 2 in a pattern generally corresponding to a chevron, extending from a region substantially adjacent nose bridge 14 toward the outer periphery 7 of the mask arrangement 2. Preferably, member 63 is oriented such that it will extend generally along the sides of a wearer's nose, and adjacent a wearer's cheek. In this manner, a variety of shapes and faces can be accommodated, with reasonable sealing and with considerable comfort. This is one of the manner in which the present invention differs from many conventional arrangements.

As indicated previously, the breathing region 12, FIG. 2, includes a nose bridge portion 14 and projection portion 16 oriented to extend over the mouth and nose of a wearer. Referring to FIG. 1, the projecting portion 16 includes aperture means therein, through which a wearer of the arrangement 1 can breath. The aperture means of the preferred embodiment, FIG. 1, is a single, relatively large centrally positioned aperture 70.

As previously discussed, the mask arrangement 1 is particularly adapted for use under high wind conditions or by riders of snowmobiles, ice boats or the like. Under these conditions, the force of air against the front of the mask member 2 may be extreme. In the absence of baffle means, such as that described below, such wind forces could jet through the aperture 70 and directly against the mouth and lower face portion of the wearer. This "jetting" of air internally of the mask arrangement 1 could not only be uncomfortable, but also potentially disruptive of free breathing.

To accommodate for this problem, and minimize the undesired jetting, the mask arrangement 1 of the preferred embodiment includes baffle means associated with the aperture means. It will be understood that many of the principles of the present invention may be applied in the absence of a baffle means. Thus, in some applications the baffle means may be absent, or it may be selectively revocable. However, in most cold-weather/high-wind applications the baffle means will probably be preferred. Referring to FIG. 1, for the preferred embodiment, the baffle means comprises a single baffle plate 75 mounted on an inside surface 76 of the mask member 2, substantially aligned with and overlapping the aperture 70. Referring to FIG. 2, the baffle plate 75 is mounted spaced from surface 76 by means of spacers 77 and pins 78. Generally, wind rushing in the mask arrangement 1, through aperture 70, will be deflected by the baffle plate 75 from directly jetting into the mouth of the wearer, as indicated by arrows 79, FIG. 1. Space between the baffle plate 75 and the inside surface 76 of the mask member 2, permits open ventilation for freedom of breathing. The baffle plate 75 is shown in FIG. 1 without stippling. The plate 75 may be made from a variety of materials including those from which the mask member 2 or eye shield 3 are formed. The baffle 75 may be transparent, as shown, but need not be.

Under cold weather conditions it may be desireable to use a heat moisture retaining member within the mask arrangement 1. Referring to FIG. 2, such a member 80 is shown mounted on an inside surface 81 of the baffle plate 75. Member 80 is retained thereon, in the preferred embodiment, by means of the pins 78.

For the preferred embodiment, member 80 is a moisture absorbent member such as a sponge or foam-type arrangement. Condensation from a wearer's breath will form within the member, which then will tend to humidify incoming air. Further, the member 80 will help retain heat from the wearer's breath, thus, warming up incoming air somewhat. It will be understood that a wide variety of members 80 may be utilized in association with the principles of the present invention. Further, the member 80 may be mounted for ease of removal, cleaning or replacement. If high winds are not anticipated, the arrangement might be used with a filter member such as member 80, but without substantial baffle means.

Excessive condensation inside of the mask arrangement 1 may result in the formation of droplets of water therein. Such droplets may drain through aperture 85, in the direction of arrow 86, FIG. 2. Should any freezing of the moisture occur near aperture 85, it will not interfere with or excessively muffle speech. Further, it may be readily cleared away. Aperture 85 is positioned so that for most wearers of assembly 1, in normal use, the excessive condensation will naturally flow downwardly thereto.

Figure 4:
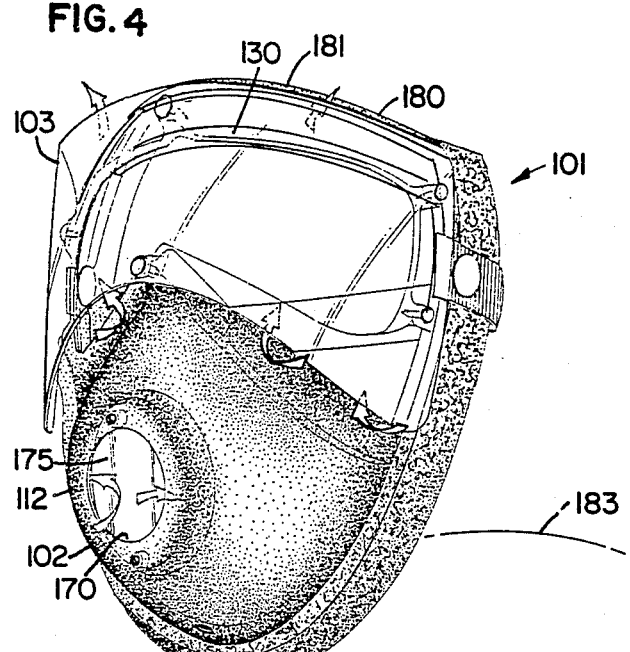
FIG. 4 is a perspective view of a first alternate embodiment of the invention.
Figure 5:
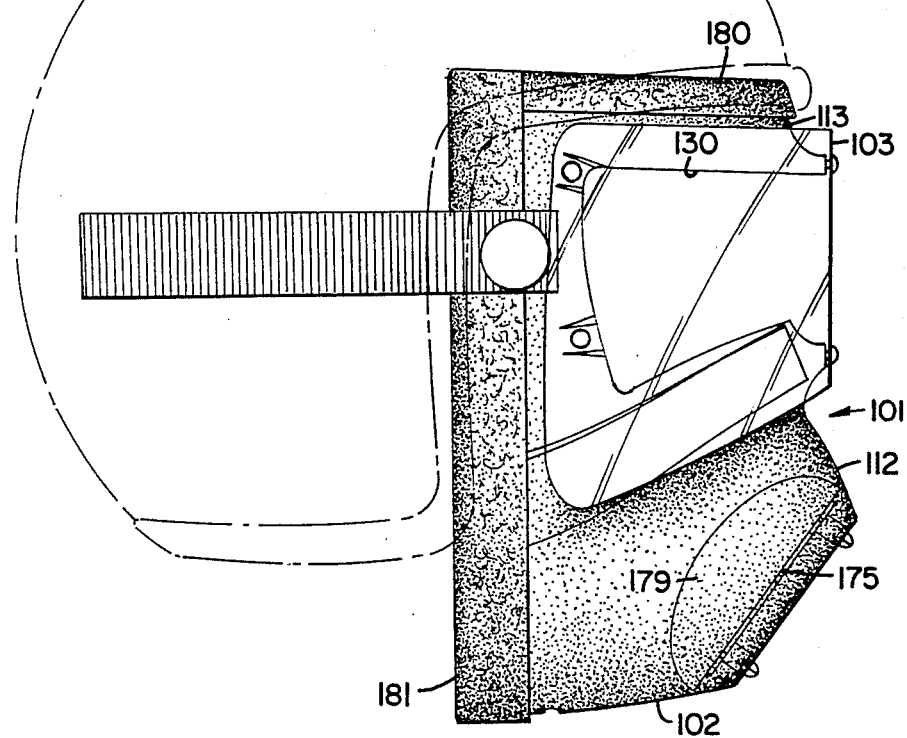
FIG. 5 is an enlarged side elevational view of a mask arrangement according to the first alternate embodiment of the present invention.

Under some circumstances, it may be desireable to wear a mask arrangement generally according to the present invention in combination with a safety helmet or the like. Such helmets generally include a forward dome which extends over and protects the forehead of a wearer. The mask arrangement 1 of FIGS. 1 through 3 would generally not be utilizable in combination with such helmets, due to the presence of the forehead dome 20 on the mask member 2. An alternate embodiment of the present invention, particularly adapted for utilization association with helmets of the like is illustrated in FIGS. 4 and 5. Referring to FIG. 5:

The reference numeral 101, FIG. 5, generally designates a mask arrangement according to a first alternate embodiment of the present invention. Generally, the features of mask arrangement 101 may be similar to or identical with mask arrangement 1, previously described, except as indicated below. Thus, mask arrangement 101 includes a mask member 102 and an eye shield 103. The mask member 102 includes a breathing region 112 and a vision region 113. The vision region includes a vision port 130 therein, overlapped by the eye shield 103. The breathing region 112 of arrangement 101 is shown having an aperture 170 therein, with a baffle plate 175 and moisture and heat retaining member 179 mounted in association therewith.

Mask arrangement 101 may include air flow directing means in association therewith analagous to that being described previously from mask arrangement 1. That is, eye shield 103 is mounted spaced from mask member 102, with surfaces directing air flow therebetween in a preferred manner.

The primary manner in which arrangement 101 differs from mask arrangement 1, is that mask arrangement 101 is devoid of the presence of an analagous forehead dome portion. Rather, mask member 102 terminates or truncates along an outer edge 180, which extends across the forehead of a wearer, in an approximate central location thereover. Edge 180, which extends substantially horizontally for a typical wearer, may include a portion of seal member 181 extending therealong to insure a snug fit with the wearer's head and face.

In FIG. 5, mask arrangement 101 is shown in operative combination with a typical protective helmet 183 shown in phantom lines. If desired, a positive seal between arrangement 101 and the protective helmet 183, not shown, may be utilized to prevent air flow therebetween.

Figure 6:
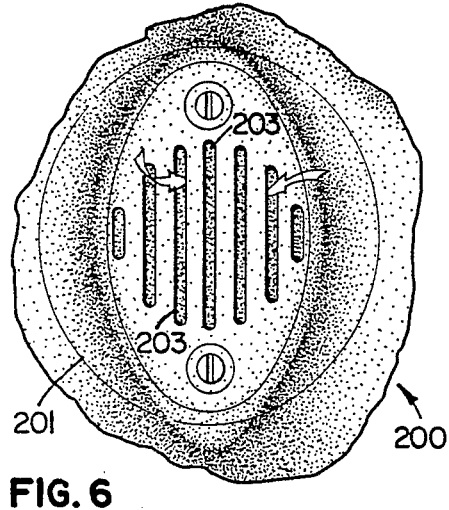
FIG. 6 is a fragmentary front elevational view of a portion of a mask arrangement according to a second alternate embodiment of the present invention.

A variety of modifications in the aperture means of the breathing region, and the baffle means associated therewith are possible in mask arrangements utilizing the principles of the present invention. Two alternate possibilities are illustrated by FIGS. 6 and 7. Such possibilities may be incorporated into mask arrangements according to either the preferred or the alternate embodiments previously described. That is, such modifications may be utilized in association with mask arrangements having forehead domes thereon, or mask arrangements designed for use in association with helmets and the like.

Referring to FIG. 6, one such modification is illustrated for mask arrangement 200, shown in a fragmentary view. In FIG. 6, mask arrangement 200 is shown in a front elevational view. For mask arrangement 200, the aperture means in breathing region 201 comprises a plurality of slits 203, rather than a single open aperture. For the embodiment of FIG. 6, the slits 203 are shown extending generally vertically. However, it will be understood that angled, or horizontal, slits may be utilized. Further, a grid pattern, not shown, may also be used as an alternate aperture means.

Except as indicated above, the embodiment of FIG. 6 may be generally as previously described for the embodiment of FIGS. 1 through 3, or the alternate embodiment of FIGS. 4 and 5. That is, the arrangement includes a mask member, an eye shield and air flow directing means generating a flow of air between the two, to generally inhibit fogging of the eye shield.

Yet another alternate embodiment of the present invention is illustrated by FIG. 7. In FIG. 7 alternate mask arrangement 225 is shown in a fragmentary cross-sectional view, generally from an orientation analagous to that used for FIG. 2, but with only a breathing region 226 shown. It will be understood that the remainder of alternate arrangement 225 may be generally analagous to either that of the embodiment of FIGS. 1 through 3, or FIGS. 4 and 5, as necessary. For the alternate embodiment of FIG. 7, the baffle means includes a baffle plate 228 mounted on a front or outside surface 229. Thus, the baffle plate 228 is mounted exterior of the mask, rather than the interior as previously described. If desired, the baffle means may include first and second baffle plates, one mounted interior and one mounted exterior, to further deflect flow and protect the wearer. While the alternate arrangement 226 of FIG. 7 is shown having a single breathing aperture 230 therein, the aperture means of FIG. 7 may be varied, for example according to the principles previously described for the embodiment of FIG. 6. In FIG. 7 a filter 270 is shown, mounted interior of the mask. It will be understood that both inner and outer baffle plates may be used, if desired.

The invention may include a shroud or outer filter, not shown, in association with the baffle plate 228. For example, upper edges and sides of the plate 228 may be enclosed or shrouded to more completely modify air flow into aperture 230. Such a shroud would partially block passage of air between the baffle plate 228 and the mask member outside surface 229. Shrouds of various sizes and shapes may be utilized in cooperation with a mask arrangement according to the present invention.

The mask members of the embodiments previously described have generally been of unitary or one-piece construction, generally molded by either vacuum molding or injection molding techniques. It will be understood that under certain circumstances it may be desireable to manufacture the mask member in more than one section, operatively combined for use. Such an arrangement may utilize the general principles of the present invention including the spaced eye shield, the air flow directing means, and the isolated breathing region with aperture means and baffle means. The mask arrangements described herein may be readily adapted for use in association with neck coverings or the like, for example by the provision of snaps or other fastening means oriented to engage such coverings.

Figure 8:
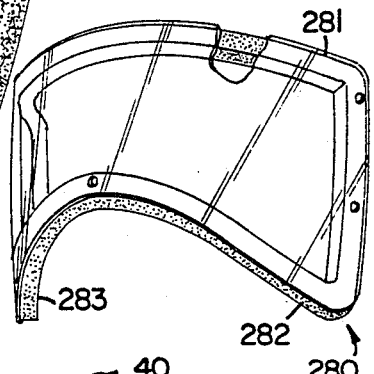
FIG. 8 is a fragmentary perspective view of an alternate form of an eyeshield according to the invention, with a portion broken away to show detail.

In FIG. 8, an optional eye shield 280 is shown. Eye shield 280 is generally as previously described and may be mounted, for example, over a vision part of either the embodiment of FIGS. 1–3 or that of FIGS. 4 and 5. Eye shield 280 has an outer periphery 281 with filter means 282 mounted thereon. The filter means 282 is a porous particle filter 283 oriented to prevent particulate matter from flowing into a gap between the shield 280 and an associated mask member. While such a filter 283 will disrupt smooth air flow somewhat, it may be desirable when particulate matter is more of a problem than fogging. Also, member 283 may be made sufficiently porous to allow some defogging flow.

It is to be understood that while certain embodiments of the present invention have been illustrated and described, the invention is not to be limited to the specific forms or arrangement of members herein described and shown, except as limited by the claims.

What is claimed and desired to be secured by Letters Patent is as follows:

1. A mask arrangement for protecting the face of a wearer; said mask arrangement comprising:
   (a) a substantially rigid mask member having inner and outer surfaces, an outer periphery and defining a breathing region and a vision region;
      (i) said breathing region being constructed and arranged to receive a nose and mouth of the wearer and including a nose bridge portion thereat;
      (ii) said vision region being constructed and arranged to align with eyes of a wearer; said vision region defining an open vision port in said mask member;
   (b) first seal means selectively sealing and insulating said breathing region from said vision region when said mask arrangement is worn;
   (c) a head strap for retaining said mask over the face of a wearer;
   (d) an eye shield mechanism including an eye shield and mounting means;
      (i) said eye shield being constructed and arranged to substantially overlap said vision port; said eye shield having inner and outer surfaces, a top edge, and a bottom edge;
      (ii) said mounting means mounting said eye shield on said mask member outer surface and spaced therefrom;
   (e) an air flow directing means including first and second lateral concave members positioned on said mask member outer surface and extending along said mask member outer surface from opposite sides of said nose bridge portion;
      (i) each of said concave members being aligned with said eye shield lower edge to direct air flow under said eye shield lower surface, upwardly across said eye shield inner surface and outwardly from said eye shield upper surface;
   (f) whereby, in use, air flow directed against said mask arrangement may be partially deflected between said mask member and said eye shield to ventilate said vision port and help prevent fogging of said eye shield inner surface; and,
   (g) whereby said breathing region is isolated from said vision region, so as not to be in substantial ventilation air flow engagement with said vision port.

2. The mask arrangement according to claim 1 wherein:
   (a) said breathing region includes central breathing aperture means therein; and
   (b) said mask arrangement includes baffle means therein in association with said central breathing aperture means.

3. The mask arrangement according to claim 2 wherein:
   (a) said baffle means includes a baffle member mounted on said mask member inner surface and spaced therefrom, said baffle member being in overlapping association with said breathing aperture means.

4. The mask arrangement according to claim 3 wherein:
   (a) said breathing region includes a heat and moisture retaining filter therein; and
   (b) said breathing region includes a condensation drainage aperture.

5. A mask arrangement for protecting the face of a wearer; said mask arrangement comprising:
   (a) a substantially rigid mask member having a breathing region, a vision region and a central portion;
      (i) said breathing region being constructed and arranged to receive a nose and mouth of the wearer;
      (ii) said vision region being constructed and arranged to align with eyes of a wearer; said vision region defining an open vision port in said mask member;
      (iii) said mask member including a nose bridge portion in said central portion;
   (b) first seal means selectively sealing and insulating said breathing region from said vision region when said mask arrangement is worn;
   (c) retaining means for retaining said mask over the face of a wearer;
   (d) an eye shield mechanism including an eye shield and mounting means;
      (i) said eye shield being constructed and arranged to permit viewing therethrough and to substantially overlap said vision port;
      (ii) said mounting means mounting said eye shield on an outside of said mask member and including a spacer mechanism for spacing said eye shield from said mask member;
      (iii) said eye shield having an upper edge, a lower edge, an inner face and an outer face; and, said eye shield comprising a single shield member positioned to extend across both eyes of a wearer;
   (e) air directing means for directing a portion of air flow against said mask arrangement first underneath said eye shield lower edge, then along said eye shield inner face, and finally and outwardly along said eye shield upper edge;
      (i) said air directing means including first and second lateral concave members positioned in said mask arrangement on opposite sides of said nose bridge portion;

(ii) each of said concave members being aligned with said eye shield lower edge to direct air flow upwardly across said eye shield inner surface;

(f) whereby in use air flow directed against said mask arrangement may be used to ventilate said vision port and help retain said eye shield clear; and, (g) whereby said breathing region is isolated from said vision region, so as not to be in substantial ventilation air flow engagement with said vision port.

6. The mask arrangement according to claim 5 wherien:

(a) said shield member is spaced a substantially constant distance from said mask member along said eye shield upper edge.

7. The mask arrangement according to claim 6 wherein:

(a) said distance of spacing of said eye shield upper edge from said mask member is between about ¼ inch and ½ inch.

8. A mask arrangement according to claim 7 wherein:

(a) said substantially rigid mask member includes a breathing region; said breathing region being constructed and arranged to receive a nose and mouth of the wearer; and, (b) said mask arrangement includes first seal means selectively sealing and insulating said breathing region from said vision region when said mask arrangement is worn;

(c) whereby said breathing region is isolated from said vision region, so as not to be in substantial air flow engagement with said vision port means.

9. A mask arrangement for protecting the face of a wearer; said mask arrangement comprising:

(a) a substantially rigid mask member having a vision region and a central nose bridge region; said vision region being constructed and arranged to align with eyes of the wearer; said vision region defining open vision port means in said mask member;

(b) an eye shield mechanism including eye shield means and mounting means;
  (i) said eye shield means being constructed and arranged to permit viewing therethrough and to substantially overlap said vision port means;
  (ii) said mounting means mounting said eye shield means on an outside of said mask member and including a spacer mechanism for spacing said eye shield means from said mask member;
  (iii) said eye shield means having an upper edge portion, a lower edge portion, an inner face and an outer face;
  (iv) said eye shield means comprising a single eye shield member positioned to extend across both eyes of a wearer; and, (c) air directing means for directing a portion of air flow against said mask arrangement: first underneath said eye shield means lower edge portion; then along said eye shield means inner faces; and finally and outwardly along said eye shield upper edge;
  (i) said air directing means including concave means positioned along and aligned with said eye shield means lower edge portion to direct air flow upwardly across said eye shield means inner surface;
  (ii) said concave means comprising first and second lateral concave members positioned in said mask arrangement on opposite sides of said nose bridge portion;

(d) whereby in use air flow directed against said mask arrangment may be used to ventilate said vision port means and help retain said eye shield clear.

* * * * *